United States Patent
Dorn

(10) Patent No.: US 10,191,626 B2
(45) Date of Patent: Jan. 29, 2019

(54) SYSTEM FOR MANAGING AND PROCESSING DATA FROM A MEDICAL FACILITY

(71) Applicant: Siemens Aktiengesellschaft, Munich (DE)

(72) Inventor: Karlheinz Dorn, Kalchreuth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 329 days.

(21) Appl. No.: 14/515,593

(22) Filed: Oct. 16, 2014

(65) Prior Publication Data
US 2015/0234557 A1 Aug. 20, 2015

(30) Foreign Application Priority Data
Feb. 20, 2014 (EP) .................................... 14156001

(51) Int. Cl.
G06F 3/0484 (2013.01)
G06F 19/00 (2018.01)
G16H 15/00 (2018.01)

(52) U.S. Cl.
CPC .......... *G06F 3/0484* (2013.01); *G06F 19/321* (2013.01); *G16H 15/00* (2018.01)

(58) Field of Classification Search
CPC ... G06F 3/0484; G06F 19/321; G06F 19/3487
See application file for complete search history.

(56) References Cited

U.S. PATENT DOCUMENTS

| | | | |
|---|---|---|---|
| 7,702,719 B1 | 4/2010 | Betz et al. | |
| 7,917,888 B2 * | 3/2011 | Chong | G06F 8/20 717/102 |
| 2001/0034771 A1 * | 10/2001 | Hutsch | G06F 9/541 709/217 |
| 2001/0041991 A1 * | 11/2001 | Segal | G06F 19/321 705/3 |
| 2001/0051881 A1 * | 12/2001 | Filler | G06F 19/3418 705/3 |
| 2006/0095443 A1 * | 5/2006 | Kumar | G06F 17/3089 |

(Continued)

OTHER PUBLICATIONS

Shyamal Patel, Hyung Park, Paolo Bonato, Leighton Chan, and Mary Rodgers, "A Review of Wearable Sensors and Systems With Application in Rehabilitation", published to http://www.jneuroengrehab.com/content/9/1/21 on Apr. 20, 2012 and retrieved Jul. 18, 2017.*

*Primary Examiner* — Shourjo Dasgupta
(74) *Attorney, Agent, or Firm* — Harness, Dickey & Pierce, P.L.C.

(57) ABSTRACT

A system for managing and processing data in a medical facility is specified. The system includes at least one browser application for running on a user device. The browser application is set up to display data record lists containing a respective list entry for a number of medical data records of at least one particular data type and individual list entries for inspection and processing. The browser application has a multilayer component architecture having a frame layer, a view layer, a view model layer, a model layer and a driver layer. In this case, the components of the view model layer are generic, that is to say independent of the data type.

16 Claims, 6 Drawing Sheets

(56) References Cited

U.S. PATENT DOCUMENTS

| | | | |
|---|---|---|---|
| 2006/0288301 A1* | 12/2006 | Hood | G06F 9/4443 |
| | | | 715/762 |
| 2009/0036105 A1* | 2/2009 | Carion | H04L 67/10 |
| | | | 455/414.1 |
| 2009/0157627 A1* | 6/2009 | Arthursson | G06F 9/45504 |
| 2010/0114951 A1* | 5/2010 | Bauman | G06F 19/321 |
| | | | 707/770 |
| 2013/0117696 A1* | 5/2013 | Robertson | G06F 19/3418 |
| | | | 715/763 |
| 2013/0197941 A1* | 8/2013 | Cochran | G06F 19/322 |
| | | | 705/3 |
| 2014/0032759 A1* | 1/2014 | Barton | H04L 67/10 |
| | | | 709/225 |
| 2014/0047560 A1* | 2/2014 | Meyer | G06F 21/62 |
| | | | 726/28 |
| 2014/0081663 A1* | 3/2014 | Calandro, II | G16H 10/60 |
| | | | 705/3 |
| 2014/0109115 A1* | 4/2014 | Low | G06F 9/541 |
| | | | 719/328 |
| 2014/0132413 A1* | 5/2014 | Fox | A61B 5/0022 |
| | | | 340/573.1 |
| 2014/0236922 A1* | 8/2014 | Boyer | G06F 19/322 |
| | | | 707/722 |
| 2015/0024351 A1* | 1/2015 | Landwehr | G09B 5/06 |
| | | | 434/169 |
| 2015/0026719 A1* | 1/2015 | Menon | H04N 21/2668 |
| | | | 725/34 |

* cited by examiner

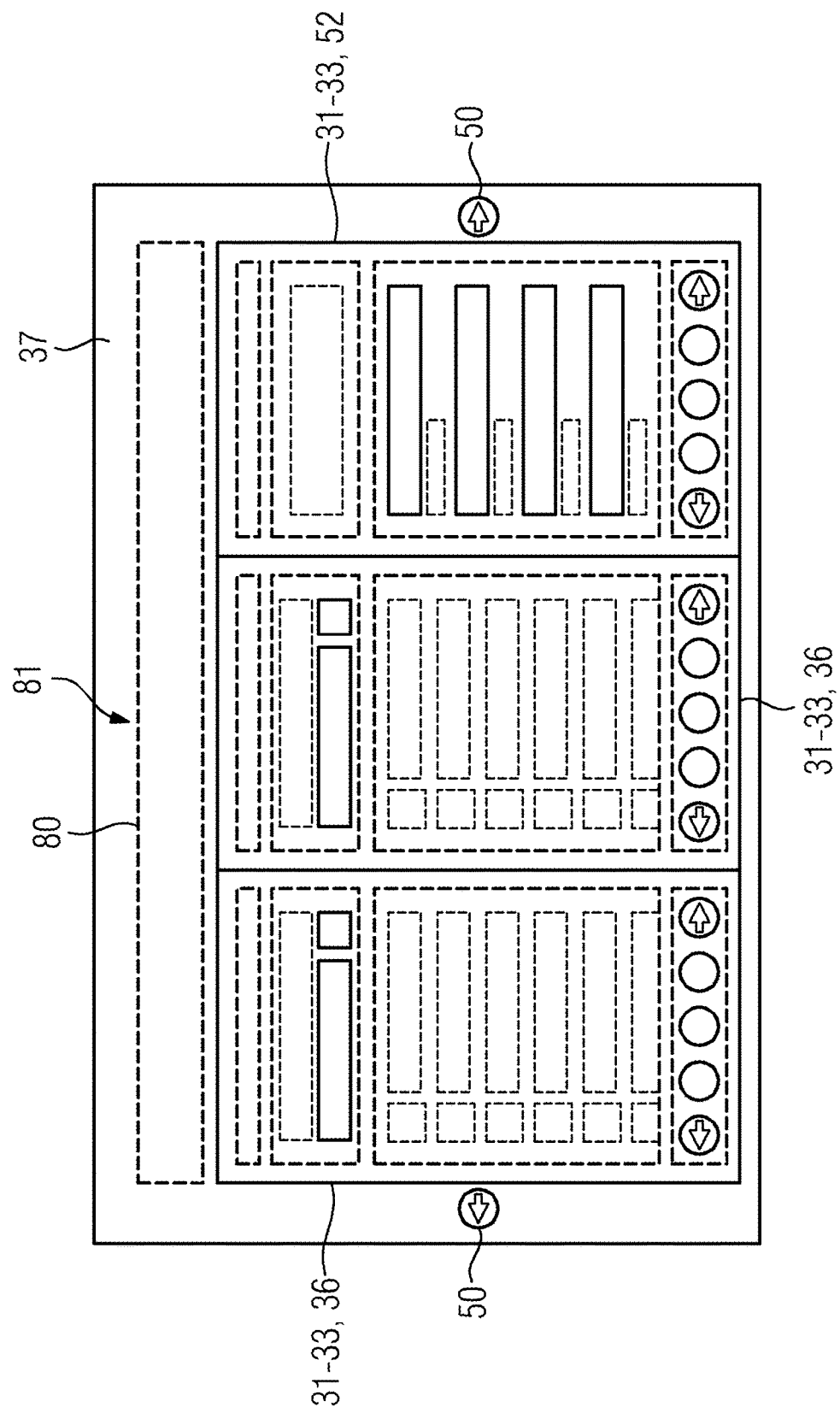

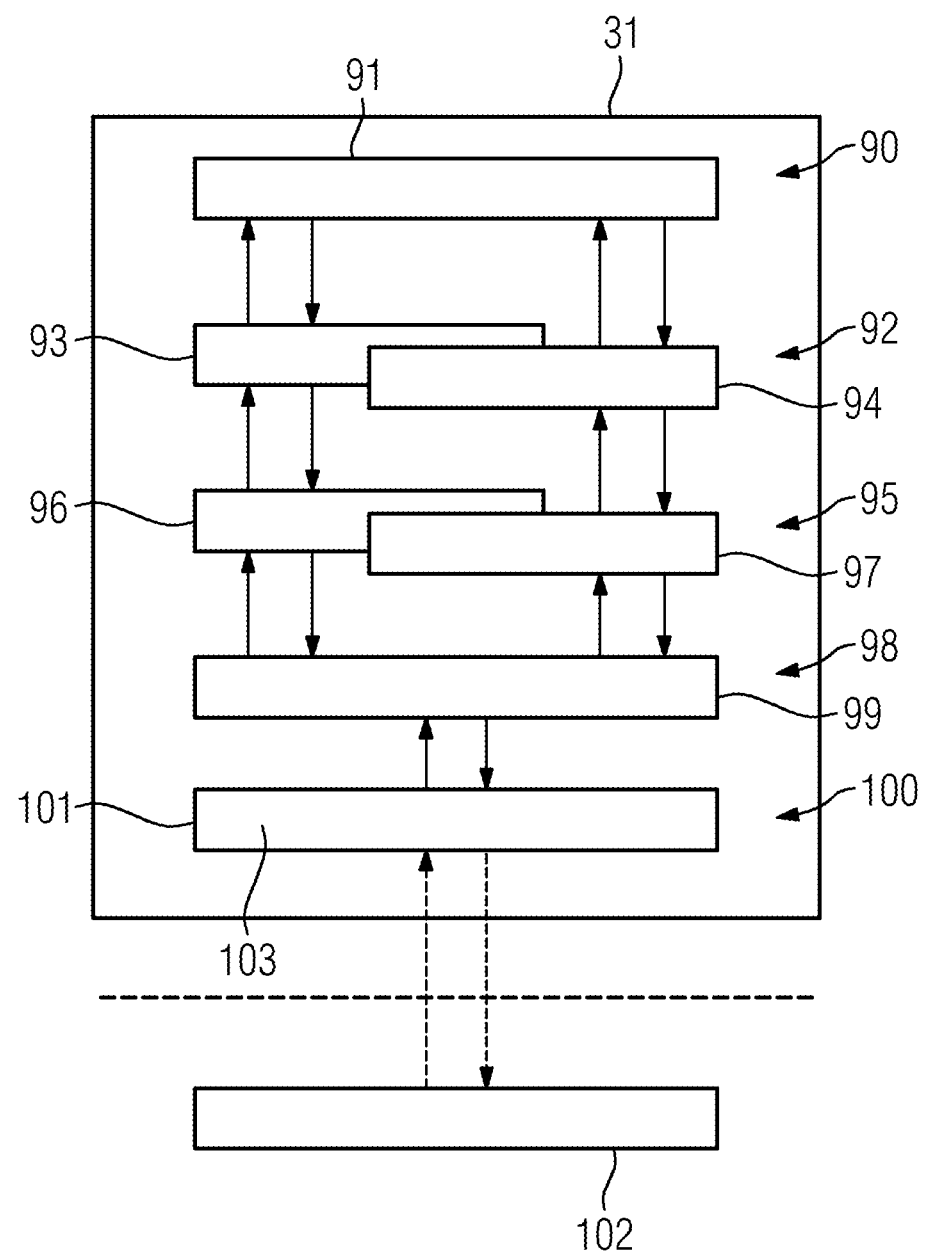

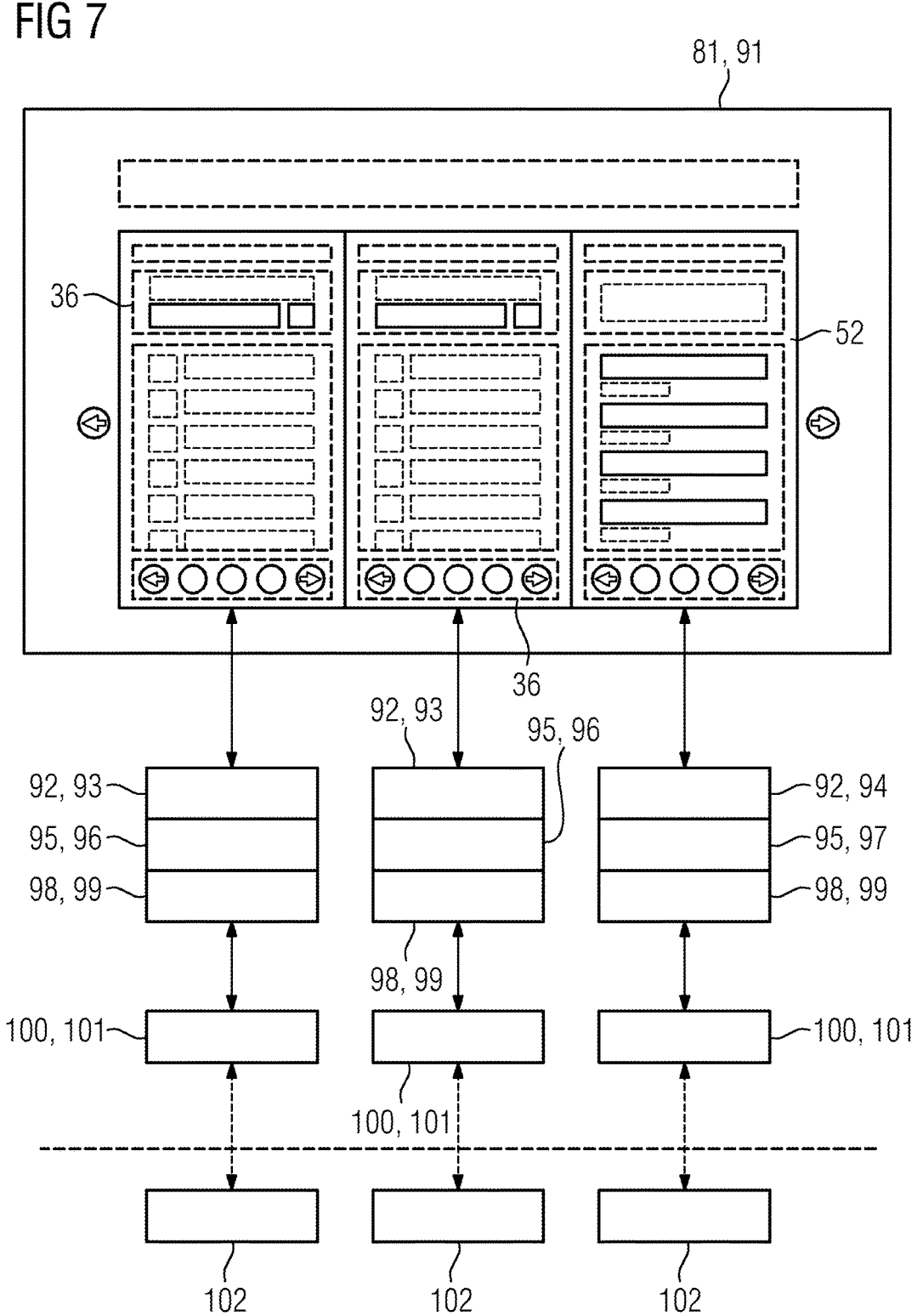

SYSTEM FOR MANAGING AND PROCESSING DATA FROM A MEDICAL FACILITY

PRIORITY STATEMENT

The present application hereby claims priority under 35 U.S.C. § 119 to European patent application number EP 14156001.1 filed Feb. 20, 2014, the entire contents of which are hereby incorporated herein by reference.

FIELD

At least one embodiment of the invention generally relates to a system for managing and processing data in a medical facility.

BACKGROUND

Here and below, the term "managing" is understood as meaning, in particular, the archiving of the data (that is to say the practice of putting the data into a persistent data memory), the reproduction (display) of the data and the deletion of the data from the data memory as well as the process of sorting and finding particular data items from the data memory in accordance with predefined criteria (browsing).

Here and below, the term "processing" is understood as meaning, in particular, the changing (editing/preparation) of the data.

The data to foe managed and processed in the medical facility comprise, in particular, patient data, tasks (works/tasks) or task lists (work lists) fox the staff in the medical facility and medical image data.

Such medical data are increasingly being managed in a computer-aided manner by server systems, in particular so-called information systems. An information system regularly comprises

- one or more data memories, for example in the form of a Storage Area Network (SAM),
- one or more associated data servers,
- at least one relational database which is implemented in a database server,
- and generally one or more further servers in which methods for accessing the database and processing the data are implemented.

Different information systems have become established for the different data types in the medical field. A "hospital information system" (HIS) for managing and processing the patient data and a "radiology information system" (RIS) for scheduling radiological examinations, assisting with the diagnosis of medical image data and documenting the findings are therefore usually used in the environment of a medical facility, for example a clinic. In addition, the IT structure of a hospital generally comprises a so-called "picture archiving and communication system" (PACS) for archiving and transmitting medical image data on the basis of the DICOM standard and an "advanced visualization (AV) system" which provides server-assisted functions for visualizing volume data, in particular dynamic volume rendering.

In this case, the server systems referred to above are generally parallel to one another. This requires a high procurement and maintenance expenditure which can hardly be managed, in particular for small medical facilities or other facilities with a comparatively small financing volume.

The above-described complex IT structure of a modern medical facility also has only comparatively poor scaling properties. Therefore, such an IT structure can usually be adapted to relatively great changes in the volume of data to be processed and archived and/or in the required computing power only with a very large amount of effort.

Personal computers (PCs) have previously been predominantly used as user devices or terminals (conventionally referred to as clients) of such an IT structure, these PCs often being in the form of so-called "thin clients" which obtain a large part of the required computing power from a connected server. However, recently, there is an increasing desire to also use mobile microcomputers, such as smartphones, tablets or PDAs, as the user device.

Another problem of conventional information systems in the medical environment is that the front-end software of these systems is often oriented specifically and rigidly to the management and processing of particular data types. This results in the front end for each information system having to be specifically programmed and maintained. This in turn makes it difficult, in particular, to integrate novel user devices such as smartphones and tablets in the clinical workflow since the diversification of the software components which is associated with the corresponding adaptation of the respective front ends can be managed only with great expenditure in terms of the production and further development expenditure.

As an alternative to conventional client-server architectures, so-called cloud solutions have become increasingly established in recent years. In this case, a "cloud" is understood as meaning a data processing device which is provided and operated by a cloud operator ("cloud vendor") independent of the user. In this case, the "cloud vendor" provides a multiplicity of users with the hardware and possibly the software of the cloud as a service as part of a license agreement (subscription). Depending on the scope of the services provided, a distinction is made between

- a use pattern which is referred to as an "infrastructure as a service" (IaaS) and in which the user is provided only with computer hardware (computers, networks and memories) of the cloud, while the user himself is fully responsible for the software operated in the cloud,
- a use pattern which is described as a "platform as a service" (PaaS) and in which the user is offered the computer hardware together with a programming and runtime environment based thereon from the cloud, with the result that the user himself is responsible only for the application software (applications) implemented in this programming and runtime environment, and
- a use pattern which is referred to as "software as a service" (SaaS) and in which the user is also provided with particular application software from the cloud.

Depending on the user group to which the respective cloud is addressed, a distinction is also made between

- a so-called public cloud whose services can be used by everyone, and
- a so-called private cloud which is accessible only to users of a particular organization, in particular a particular corporation.

For each user of a public cloud, the access authorizations to particular hardware and software components of the cloud are controlled by the subscription assigned to the user. As a result, public clouds are usually "multi-client capable" (multi-tenant). This refers to the ability to keep data, user management and computing operations strictly separate for users with a different subscription. A user of the public cloud therefore cannot look at the data, user management and computing operations of another user with a different subscription and also cannot influence these data.

SUMMARY

At least one embodiment of the invention is directed to a system for managing and processing data in a medical facility, which system can be used in a particularly flexible manner, in particular is particularly scalable.

Advantageous refinements and further developments of the invention which are partially inventive per se are explained in the subclaims and the following description.

The system according to at least one embodiment of the invention is used, in particular, to display and process medical data records of one of the following data types:
 patient data comprising personal and medical details of a particular patient of the facility, in particular details of the name, the address, the age, the gender, previous diagnoses and treatments,
 tasks (works/tasks) and task lists (work lists) which need to be carried out by one or more medical users (doctors, medical assistants, nurses, etc.) in the medical facility, and
 context data, that is to say context information relating to medical image data, in particular references to the storage location of image data records and optionally met a data relating to image data records, for example the recording parameters on which the respective image recording is based.

The data records of a particular data type are also referred to as a "resource" below.

The system comprises at least one browser application for running on a user device. In this case, the or each browser application is set up, on the one hand, to display data record lists containing a respective list entry for a number of medical data records. These data record lists—referred to as "feed" below—are, in particular (but not necessarily), the result of a search for data records having particular properties, for example for patient data records relating to patients with a particular surname.

BRIEF DESCRIPTION OF THE DRAWINGS

Example embodiments of the invention are explained in more detail below using a drawing, in which:

FIG. 5 shows, in an illustration according to FIG. 3, a variant of the browser application which is intended to run on a personal computer, a notebook or a tablet computer and in which a plurality of GUI pages of the user interface can be presented at the same time, FIG. 6 shows a schematic block diagram of the component architecture of the browser application according to FIGS. 3 and 4 or of the browser application according to FIG. 5, and FIG. 7 shows a schematic block diagram of the browser application according to FIG. 5.

Mutually corresponding parts and variables are always provided with the same reference symbols in all figures.

DETAILED DESCRIPTION OF THE EXAMPLE EMBODIMENTS

Figure 1:
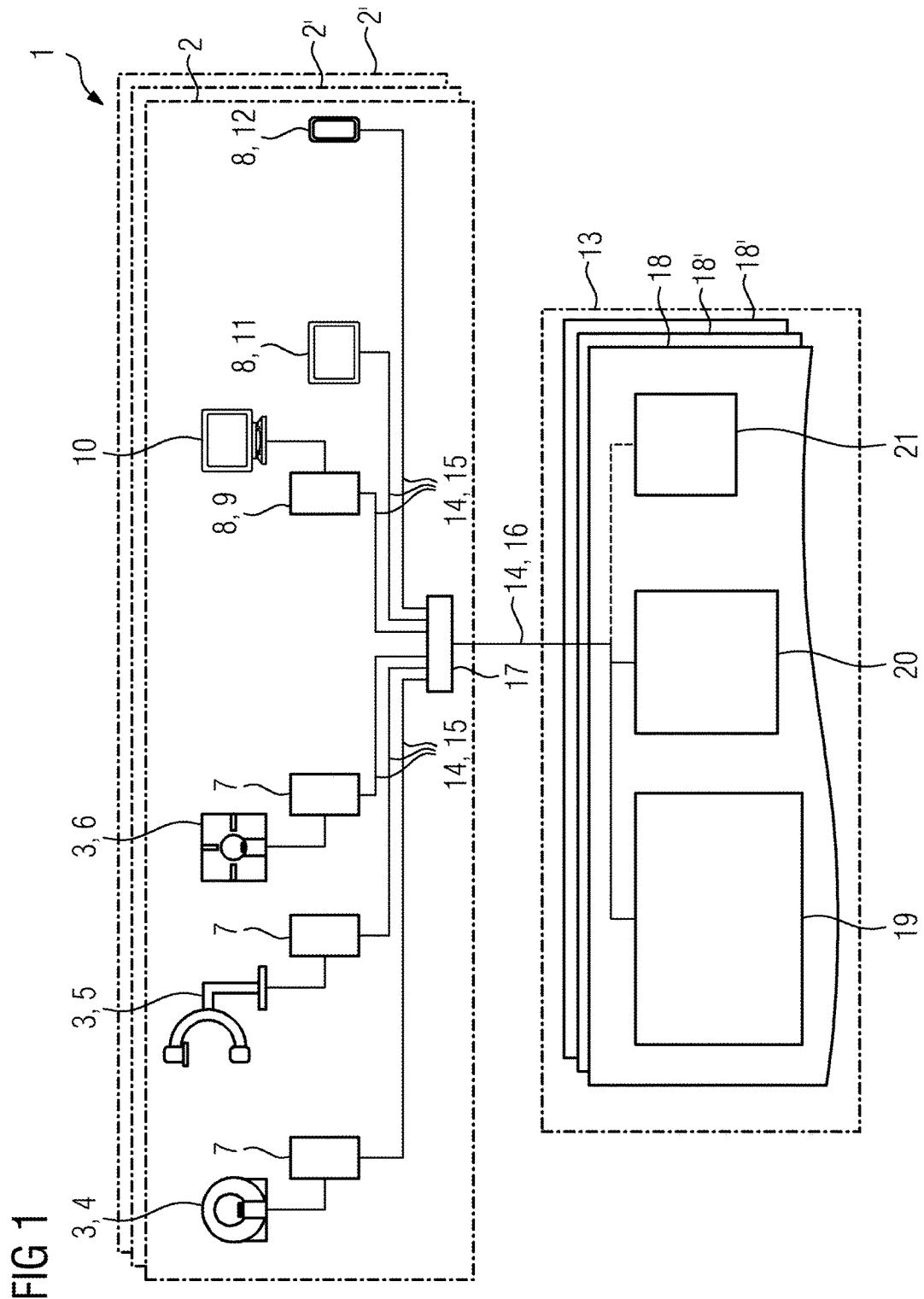
FIG. 1 shows a schematic block diagram of a system for managing and processing data in a medical facility, having a plurality of modalities and user devices or terminals (devices) and having a public cloud which is connected to the modalities and devices via the Internet.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program, code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and ail combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantifies. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that, perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may foe otherwise oriented (rotated 90 degrees or at other orientations) and the spatially relative descriptors used herein are interpreted accordingly.

Although the terms first, second, etc. may foe used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The system according to at least one embodiment of the invention is used, in particular, to display and process medical data records of one of the following data types:

patient data comprising personal, and medical details of a particular patient of the facility, in particular details of the name, the address, the age, the gender, previous diagnoses and treatments, tasks (works/tasks) and task lists (work lists) which need to be carried out by one or more medical users (doctors, medical assistants, nurses, etc.) in the medical facility, and context data, that is to say context information relating to medical image data, in particular references to the storage location of image data records and optionally meta data relating to image data records, for example the recording parameters on which the respective image recording is based.

The data records of a particular data type are also referred to as a "resource" below.

The system comprises at least one browser application for running on a user device. In this case, the or each browser application is set up, on the one hand, to display data record lists containing a respective list entry for a number of medical data records. These data record lists—referred to as "feed" below—are, in particular (but not necessarily), the result of a search for data records having particular properties, for example for patient data records relating to patients with a particular surname.

The or each browser application is also set up to display the contents of individual list entries (referred to as "tweet" below) for inspection or processing. Each tweet may completely or partially contain the contents of the associated data record itself, for example the surname, first name, address, etc. of a patient in the case of patient data, with the result that the data record may be completely or partially identical to the associated tweet. However, in the case of data records with a large storage requirement in particular, the data record or individual components of the latter is/are preferably stored separately from the associated tweet. In this case, instead of the information in the data record, the tweet associated with a data record comprises one or more links (in particular in the form of a URL) which can be used to access the data record or individual components of the latter. Furthermore, the tweet, associated with a data record often also comprises links (again preferably in the form of a URL) which refer to the storage location, of an associated different data record. For example, the tweet associated with a patient data record of a patient usually contains links to tasks and/or context data records which are likewise linked to this patient.

The or each browser application is preferably used to selectively and solely display and process data records of a specific data type, with the result that different browser applications are provided, for example, for managing and processing patient data, on the one hand, and for displaying and processing task lists, on the other hand. However, embodiments of the browser application which are provided for the purpose of managing and processing data records of a plurality of data types are also within the scope of the invention.

According to at least one embodiment of the invention, the browser application is subdivided into five layers in terms of its component architecture. These layers comprise—according to their rank order from "top" to "bottom" (that is to say from the presentation and user interaction level to the data access level)—a frame layer, a view layer, a view model layer, a model layer and a driver layer.

The frame layer preferably comprises exactly one component. In an expedient embodiment, the component of the frame layer ("frame component" below) is a generic runtime container for the GUI pages defined by the components of the view layer. To the outside, the "frame component" is presented in this case either as a native application which is independently executable on the operating system, of the user device, for example in the form of an iOS app, phone-gap-exe or Windows 8 app. However, it may alternatively also be set up to run in a web browser and may be in the form of an HTML5 program, for example, in this variant. The frame component is therefore preferably used as a software adapter between the or each GUI page and the runtime environment of the application, in particular the operating system of the user device or a web browser.

The frame component defines a number and arrangement of (GUI) pages of a graphical user interface (GUI) which are to be displayed at the same time, each of these GUI pages being used either to display a respective feed (that is to say a list of tweets) or to display the contents of a tweet. In this case, a closed part of a graphical user interface which is functional per se is referred to as a GUI page, which part—for instance in the form of a window—can be operated either alone or together with further GUI pages. The or each frame component also comprises functions for transferring control between different GUI pages. In this case, an action which is manually caused by a user or is automatically caused by the system and by which a GUI page is activated (released for user interaction) or deactivated (blocked for user interaction), is displayed on the screen or is hidden from the screen is referred to as control transfer.

In this case, the or each frame component may either be invisible from the user's point of view or may itself form a superordinate part of the graphical user interface of the browser application and in this case may literally frame, in particular, the or each GUI page displayed.

As a result of the fact that the frame component determines the number and arrangement of GUI pages displayed, the type of control transfer and possibly a part of the graphical user interface of the browser application, it defines—depending on the type of user device—an application style adapted to this user device. For example, according to a frame component provided for the purpose of executing the browser application on a tablet computer, three GUI pages for a respective feed or tweet are respectively displayed beside one another in an active area of the screen surface, in which case the row of GUI pages can be pulled over the screen by manually swiping across the touchscreen of the tablet computer, as a result of which GUI pages at the edge can be pushed out of the active area (and therefore deactivated and hidden) and other GUI pages can be pushed into the active area (and therefore activated and displayed). In contrast, according to a frame component provided for the purpose of executing the browser application on a smartphone, only one GUI page for a respective feed or tweet is displayed at any time, in which case manual swiping across the touchscreen or a particular actuation of a control element is again provided, for example, for changing between different GUI pages.

The view layer comprises a number of components, that is to say at least one component but preferably two or more components. Each component, of the view layer specifically respectively defines, for a particular data type, the graphical contents of a GUI page for displaying a feed or for displaying a tweet. In one expedient embodiment, the view layer comprises, for each data type to which the browser application is oriented, a respective component (referred to as "<Resource>ListView" by way of example) which defines a GUI page for displaying a feed, and a further component (referred to as "<Resource>ListItemView" by way of example) which defines a GUI page for displaying a tweet.

A corresponding browser application for solely managing and processing patient data therefore contains two components (namely "<Patient>ListView" and "<Patient>ListItemView") in the view layer.

In this case, each component of the view layer defines, in particular, the type, the appearance and arrangement of the graphical elements of the associated GUI page, in particular the control elements, which can be used to output information to a user or to receive user inputs and commands. In contrast, the components of the view layer do not stipulate the logic (UI logic) connected to the control elements since this is reserved for the components of the view model layer.

The view model layer comprises a number of components, each of which is associated with at least one component of the view layer. As indicated above, each component of the view model layer implements the UI logic, that is to say the functional properties and commands for the control elements of the GUI page defined in the associated component of the view layer. In an expedient embodiment, the view model layer comprises two components, a first component of which (referred to as "GenList-ViewModel" by way of example) implements the UI logic of a GUI page for displaying a feed, while the second component (referred to as "GenListItem-ViewModel" by way of example) implements the UI logic of a GUI page for displaying a tweet.

The model layer comprises a number of components, that is to say again at least one component. The or each component of the model layer in this case specifically defines, for a particular data type, the structure of the associated data records, in particular the variables associated with the data record.

The driver layer likewise comprises a number of components, that is to say again at least one component, but preferably two or more components. Each component of the driver layer (referred to as "driver component" below) is set up in this case to provide data access by the superordinate layers to a particular data memory. The browser application therefore loads feeds and tweets and/or the underlying data records solely using that driver component which is oriented to the respective data memory in which the tweets and data records are stored. In this case, the data access provided by the driver components is bidirectional and therefore makes it possible for the browser application to both download (in particular asynchronously) and upload (in particular again asynchronously) feeds, tweets and possibly data records. The or each driver component establishes automatic data binding between the GUI of the browser application and the respective data memory.

The data memory may be an internal data memory, for example the main memory of the user device, or an external data memory. In the latter case, the data memory is provided, in particular, by cloud storage of a public cloud which is accessed by the associated driver component directly without using an interposed server or service. To generalize, the data memory within the scope of the invention may generally be any desired subscriber of a (wireless or wired) computer network with which medical data records and associated feeds and tweets can be interchanged, the respective driver component being able to use any desired data transmission protocol (for example also email, SMS or Twitter). If the driver layer comprises a plurality of driver components, they are preferably assigned to different data memories (for example cloud storage offered by a plurality of cloud vendors).

The view layer, the view model layer and the model layer correspond to the basic principle according to the so-called MVVM (Model View ViewModel) scheme, as is common when programming applications with a graphical user interface. However, an important difference between the component architecture according to the application and the common MVVM scheme in this case is that the components of the view model layer are generic, that is to say independent of the specific data type of the processed data records. Therefore, the same components of the view model layer can be used, in unchanged form, to process data records of different data types (for example patient data as well as task lists) or associated feeds and tweets. In this case, the generic configuration of the view model layer makes it possible to significantly reduce the production expenditure for the or each browser application. In particular, this makes it possible to completely or at least virtually automatically generate the or each browser application.

In addition, the conventional MVVM model in accordance with the teaching according to the invention is extended with two further layers, namely the frame layer and the driver layer. As a result of the frame layer added at the very top of the layer architecture, it is possible in this case to reuse a large part of the components of the browser application in unchanged form when adapting the application to different user device types (PC, smartphone, tablet, etc.), thus significantly reducing the production expenditure for the diversified application variants. As a result of the driver layer added at the very bottom of the layer architecture, with its possible plurality of exchangeable driver components, it is again possible to flexibly use the browser application with a wide variety of data memories (for example the local memory of the user device as well as the cloud storage provided by one or more public cloud vendors).

In a preferred embodiment of the system, the components of the driver layer and/or the components of the frame layer are also generic, that is to say independent of the data type of the processed data records. This makes it possible to further reduce the production expenditure for the or each browser application and likewise promotes automatic generation of the or each browser application.

The components of the view model layer preferably implement a generic CRUD (create-read-update-delete) functionality insofar as the components of the view model layer comprise functions for creating, reading, updating and deleting a feed (with tweets contained therein) which can be applied to feeds and tweets relating to data records of any desired data type. Therefore, these functions can be applied, in unchanged form, to feeds and tweets or data records of all data types managed within the scope of the system. The functions defined with respect to a tweet expediently at least partially also act on the associated data record. For example, when deleting a tweet assigned to a patient data record, this patient data record is also deleted.

The components of the view layer, the view model layer and the model layer can preferably be instantiated repeatedly. Each GUI page—displayed by the browser application or kept in the background of the GUI—of a feed or each GUI page of a tweet is expediently respectively assigned a separate instance of the associated components of the view layer, the view model layer and the model layer in this case.

The different instances of the view layer, the view model layer and the model layer are expediently executed concurrently in this case.

Furthermore, each driver component can preferably also be instantiated repeatedly, each GUI page also being assigned a separate instance of a suitable driver component. The different instances of the driver components are also expediently executed concurrently.

The driver components are preferably set up to asynchronously provide data access. The control flow between the driver components and the components of the superordinate layers is therefore configured in such a manner that the latter do not wait for the response from the driver component in the event of a query for the respective driver component.

In order to be able to adapt the browser application to different data memories which particularly little expenditure, the driver layer preferably comprises a predefined application programming interface (referred to as "driver API" below) on which all driver components of the driver layer are based.

In one particularly advantageous embodiment variant, the system comprises an application template (that is to say an application template in which a basic framework of the browser application is predefined in a configurable manner) and an application configurator. The application configurator is set up to automatically generate the or each browser application from the application template using predefined configuration information. The configuration information comprises, in particular, the following details:

- details relating to the user device on which the respective browser application is intended to run. These details comprise, for example, the designation of the device type, the designation of the operating system, etc.
- details relating to the or each data type of the data records and associated feeds and tweets which are intended to be displayed and processed using the browser application to be generated, and/or
- details relating to the or each data memory which is intended to be accessed by the respective browser application.

The application configurator uses these details to configure the application template with the respectively suitable components and thus generates the browser application.

The application configurator can be implemented by way of an independent software program which is independent of the browser application. However, the function of the application configurator is preferably integrated in the frame component. For this purpose, the application template, which is in the form of an XML file for example, and different versions of the frame component are preferably provided in a data memory, each version of the frame component being oriented to a particular user device type and possibly a particular application style (the configuration information relating to the type of user device implicitly results in this case from the choice of the suitable version of the frame component). Upon loading the respective frame component, the frame component then configures the browser application using the application template by automatically downloading suitable components of the subordinate layers.

The data memory which holds the application template and the at least one frame component is preferably cloud storage (app store) of a public cloud, from which the frame component and the application template can be downloaded onto the user device. However, the application template and/or the at least one frame component can alternatively also be held in a memory of the user device or a mobile storage medium (for example a CD-ROM or a USB stick).

FIG. 1 shows, in a rough schematic simplification, a system 1 for managing and processing medical data in a medical facility 2 which is a clinic, for example.

In terms of hardware, the system 1 comprises a number of modalities 3, that is to say imaging, medical examination devices in the facility 2. In the example illustration according to FIG. 1, the system 1 therefore comprises a computer tomograph 4, a C-arm device 5 and a magnetic resonance tomograph 6. Each modality 3 is assigned a (control and evaluation) computer 7.

In terms of hardware, the system 1 also comprises a number of user devices or terminals (devices 8 below) in the facility 2 which are used to display and process data. In the simplified example according to FIG. 1, the devices 8 comprise a personal computer 9 with a connected screen 10, a tablet 11 and a smartphone 12.

As a component which is arranged outside the facility 2, the system 1 comprises a public cloud 13. Within, the scope of the system 1, the service offered by Microsoft under the designation "Windows Azure", for example, is used as the public cloud 13. However, deviating from this, another public cloud or a combination of a plurality of public clouds (possibly also from different providers) can also be used as the public cloud 13 within the scope of the invention.

The public cloud 13 is connected to the components of the system 1 inside the facility, that is to say the modalities 3 and devices 8, via a (data transmission) network 14. This network connection is formed inside the facility 2 by an intranet 15 of the facility 2, which intranet is constructed, for example, as a so-called local area network (LAN) on the basis of wired Ethernet technology and/or as a wireless local area network (WLAN). Outside the facility 2, the network 14 is formed by the Internet 16. A firewall 17 is usually arranged at the interface between the intranet 15 and the Internet 16.

The services provided by the public cloud 13 within the scope of the system 1 are defined, by a license agreement referred to as a subscription 18. In this case, the subscription 18 controls which hardware and software components of the public cloud 13 are accessible to the components of the system 1 inside the facility. The term "subscription" 18 is therefore used below to designate that part of the public cloud 13 which is exclusively assigned to the facility 2 within the scope of the system 1. Other areas of the public cloud 13 can be allocated—as indicated in FIG. 1—to further medical facilities 2' within the scope of further subscriptions 18'. In this case, each facility 2, 2' solely has access to the data and services allocated to it according to its subscription 18, 18' but does not have access to the data and services of other facilities 2 and 2'. In this sense, the public cloud 13 is "multi-client capable" (multi-tenant). The "client" (tenant) of a subscription 18, 18' is preferably a hospital, a doctor's surgery or another medical facility. In principle, however, it is also conceivable to allocate subscriptions 18, 18' to smaller units or groups of persons through to individual patients.

According to the subscription 18, the system 1 of the facility 2 is provided with, inside the public cloud 13,
- a data memory which is referred to as cloud storage 19 below,
- a memory for applications (application software) which is referred to as an app store 20' below, and
- cloud computing services 21.

The cloud storage 19 is used to persistently store the data from the facility 2. The app store 20 provides applications, drivers and other peripheral software, for example configuration files and templates, which can be downloaded by the components of the system 1 inside the facility, that is to say the modalities 3 and the devices 8, and run on the modalities 3 (more precisely the assigned computers 7) and on the devices 8 during operation of the system 1. Within the scope of the system, the cloud computing services 21 are only optionally used fox all computing operations which are not carried out on the modalities 3 or the devices 8 themselves. The latter concerns, in particular, the computing-power-intensive preparation, of 3D image data (volume data) of the respective modality 3 for storing (preprocessing) and/or deriving rendered views V (image scenes or scene graphs) for the two-dimensional visualization (image synthesis, volume rendering) of such volume data.

Figure 2:
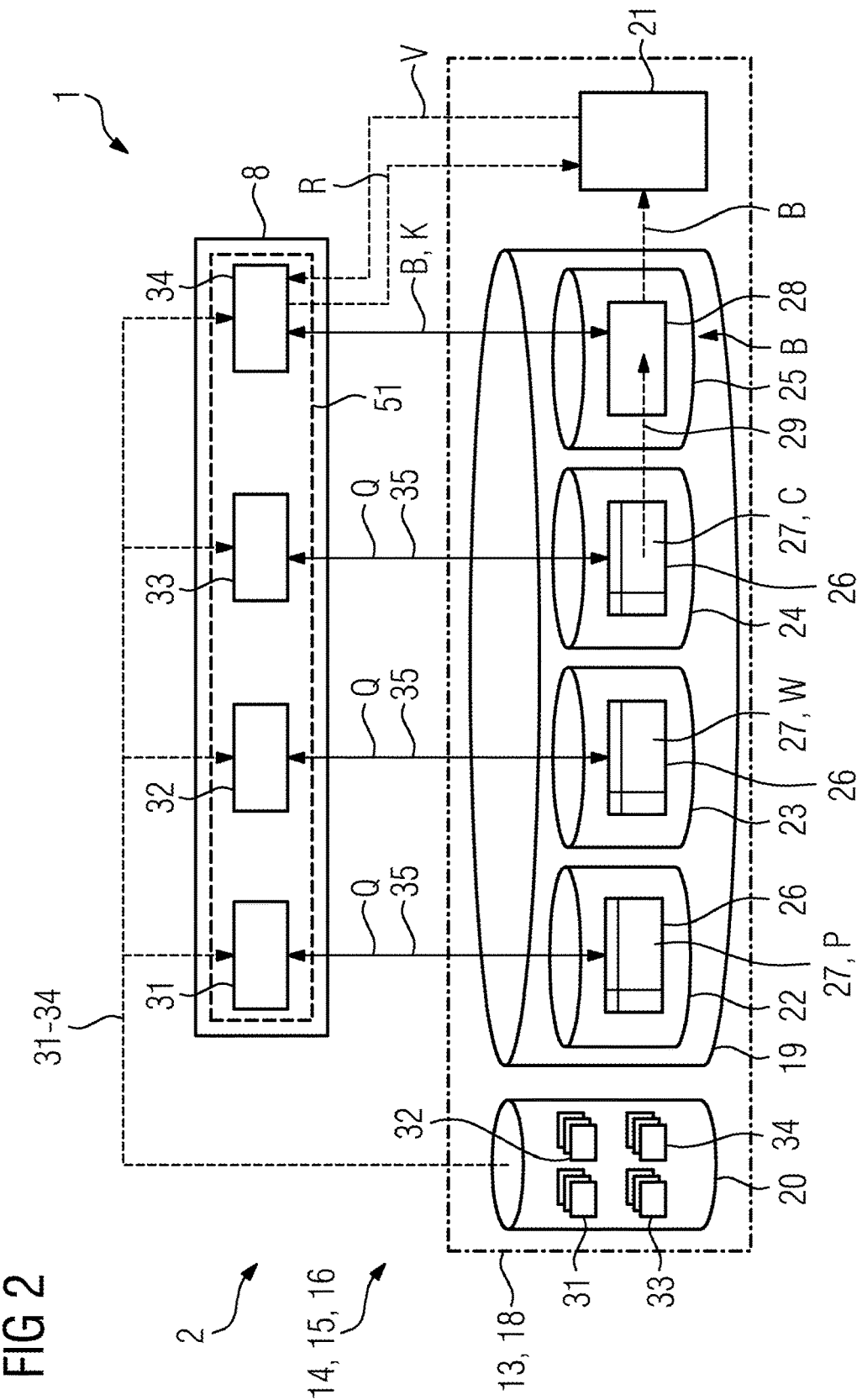
FIG. 2 shows a schematic block diagram of the software structure of the system, according to which the system respectively has specifically assigned memory areas (hubs) for different types of data in the medical facility in cloud storage of the public cloud, namely a patient hub for patient data records, a work list hub for tasks, a context hub for context data records and an image hub for image data records, the system, containing, on each device for each hub, an assigned application for accessing the data records stored in this hub, a table memory (table storage) respectively being created in the three first-mentioned hubs and containing an associated list entry (tweet) for each data record in the hub, and each application being set up to search the table memory of the associated hub (browsing) and to extract and display a data record list (feed) of selected tweets, and the application assigned to the image hub being set up to display (viewing) the image data records.

According to FIG. 2, the data to be managed and processed within the scope of the facility 2 comprise patient data records P, tasks W, context data records C and image data records B, these data specifically respectively having the contents explained in more detail above. In this case, image data records B may contain medical image data or volume data or another item of image, sound, graphics or text information (photos, videos, documents).

According to FIG. 2, a separate memory area is respectively created for each of these different data types (resources) within the cloud storage 19, which memory area is referred to as a (resource) hub below. Specifically, a (patient) hub 22 for storing the patient data records P,
a (work list) hub 23 for storing the tasks W,
a (context) hub 24 for storing the context data records C, and
an (image) hub 25 for storing the image data records B are therefore created in the cloud storage 19.

Each of the hubs 22-24 respectively contains a table memory (referred to as table storage 26 below).

Within the scope of the system 1, a list entry is created for each stored data record in the table storage 26 of the respectively assigned hub 22-24, which list entry is referred to as a tweet 27 below.

In the case of data records which, by their nature, consist of comparatively few, discrete details, the entire data record or at least a part of the latter is stored as a tweet 27 in the table storage 26 of the respective hub 22-24. In the example according to FIG. 2, this concerns the patient data records P, the tasks W and the context data records C. Instead of the table storage 26, however, the work list hub 23 may also have so-called queue storage for storing the tasks W according to a first-in-first-out principle.

In order to store the image data records B which are generally substantially formed from a relatively large and non-alphanumeric data block, so-called blob storage 28 is provided in the image hub 25 instead of table storage 26, the image data records B being stored in said blob storage as "binary large objects (BLOB)" in a form which is not structured any further. A respective context data record C in the form of a tweet 27 is stored in the context hub 24 for the image data records B stored in the image hub 25. This tweet 27 contains at least one URL 29 (uniform resource locator) which designates the storage location of the image data record B in the blob storage 28 of the image hub 25.

An application 31-34 is provided for each of the hubs 22-25 in the app store 20, which application is respectively selectively used to present and process the data records stored in the respectively assigned hub 22-25. Each of the applications 31-34 therefore represents the assigned hub 22-25 at the level of the devices 8. The applications 31-34 are therefore—in accordance with the resource hubs—also referred to as "application hubs".

Specifically, the applications provided in the app store 20 therefore comprise an application 31 for managing and processing the patient data records P stored in the patient hub 22,
an application 32 for managing and processing tasks W,
an application 33 for managing and processing context data records C, and
an application 34 for displaying and processing the image data records B stored in the image hub 25.

The applications 31-34 may be downloaded from the app store 20 onto each of the devices 8 and can be executed there. If the system 1—as illustrated in FIG. 1—comprises different types of devices (for example personal computers 9, tablet computers 11 and/or smartphones 12), different versions of the applications 31-34 which are adapted to run on the respective device 8 are respectively provided in the app store 20. However, the applications 31-34 and their variants are preferably not held in a prefabricated state in the app store 20. Rather, a common application template in the form of an XML file is stored in the app store 20 at least for the functionally similar (browser) applications 31-33, from which template the respective application is automatically generated, upon request by one of the devices 8, by way of an application configurator using predefined configuration information.

For example, the applications 31-34 for running on the tablet computer 11 and the smartphone 12 are provided in the form of an app which is adapted to the respective device type, whereas the versions of the applications 31-34 provided for the personal computer 9 are designed to run in a web browser.

In comparison with a conventional IT structure for managing medical data, the patient hub 22 and the assigned application 31 assume, for instance, the function of a conventional hospital information system (HIS) from the user's point of view. In particular, all of the personal patient data (relevant to data, protection) are included in the patient hub 22 which therefore reproduces an electronic patient file for the individual patient. The other hubs 23-25 preferably do not contain any information which per se could be assigned to a particular patient (privacy information). The work list hub 23 and the assigned application 32 are substantially an equivalent to a conventional radiology information system (RIS) for the user by virtue of the fact that they list tasks pending execution inside the facility 1. The context hub 24 and the assigned application 33 assume, for instance, the function of a conventional PACS, from the user's point of view, by virtue of the fact that the information needed to find and process image data records B is stored and can be searched there. The image hub 25 and the assigned application 34 finally assume, for instance, the function of a conventional AV system.

Although the functions contained in the hubs 22-25 and the assigned applications 31-34 are linked to one another to a high degree, each of the hubs 22-25 together with the respectively assigned application 31-34 can also be operated independently of the respective other hubs 22-25 and their applications 31-34. For example, an image data record B contained in the image hub 25 can be accessed even without the associated context data record C of the context hub 24 if the URL 29 of the image data record B to be displayed is made available to the application 34 assigned to the image hub 25 in another manner, for example by email, SMS or Twitter. Furthermore, the patient data P may also be held outside the public cloud 13 since the patient hub 22 is not required for the function of the other hubs 23-25 and the assigned applications 32-34.

The applications 31-33 are used solely to find particular data from the data memory in accordance with predefined criteria (browsing). In particular, they are not used to display large-format medical image data (viewing). At best, they may constitute so-called stamp images, that is to say very small images of medical image data records as characteristic information inside their lists. These browsing applications are now designed in such a manner that their lists are all supplied from the REST standard of the cloud storage 19, thus making it possible to dispense with a separate server service for this purpose.

The browsing application 33 assigned to the context hub 24 manages a list (feed) of entries (tweet) which together represent, for example, the examinations (study) of a patient and whose respective contents can be directly forwarded to the viewing application 34 of the image hub 25. In particular, however, the application 33 (and also the associated context hub 24) is independent of the viewing application 34 (and also the associated image hub 25). The application 33 is virtually the equivalent of a PACS browser which does not, however, look after the viewing (that is to say the image display) but rather can forward references to image data records to be displayed in the form of a tweet in each case.

The application 32 assigned to the work list hub 23 manages a list (feed) of entries (tweet) which together represent, for example, the orders (procedures) from a "client" (tenant) and whose respective contents can be directly forwarded to the application 33 assigned to the context hub 23. In particular, however, the application 32 (and also the associated work list hub 23) is independent of the application 33 (and also the associated context hub 24). The application 32 is virtually the equivalent of an RIS browser which does not, however, look after the context information but rather can forward references thereto in the form of a tweet in each case. Worded in a more abstract manner, it could be stated that the application 32 manages a list of references to context information which has a more short-term nature and typically can be processed in a snort period (for example within a day).

The application 31 assigned to the patient hub 22 manages a list (feed) of entries (tweet) which together represent, for example, the patient files of a tenant and whose respective contents can be directly forwarded to the application 32. In particular, however, the application 31 (and also the patient hub 22) is independent of the application 32 (and also the associated work list hub 23). In this case, the application 31 is virtually the equivalent of an HIS/EPR browser which does not, however, look after the work list or the context information but rather can forward references thereto in the form of a tweet in each case. Worded in a more abstract manner, it could be stated that the application 31 manages a list of references to context information which has a more long-term, permanent nature and typically represents the contexts which are experienced by a patient during his life (as a result of different examinations) and can be used as reference examinations.

The application 31 assigned to the patient hub 22 is a browser application which searches the table storage 26 of the patient hub 22 for tweets 27 which correspond to a particular search term which can be predefined by a user. In this case, in response to a search query Q (FIG. 2) from the application 31, the patient hub 22 returns, to the application 31, a data record list which is referred to as a feed 35 below and contains the tweets 27 corresponding to the search query Q. The application 31 displays the received feed 35 on the device 8 on a GUI page 36 (illustrated by way of example in FIG. 3) of a graphical user interface 37 (GUI).

Figure 3:
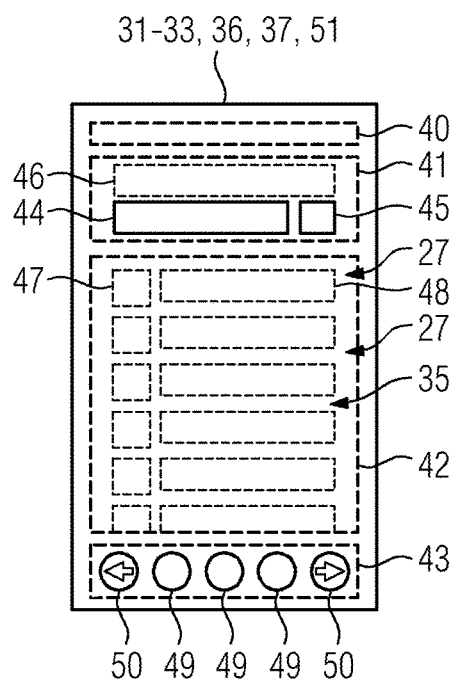
FIG. 3 shows a schematic illustration of a GUI page of a user interface (GUI) of a browser application which is intended to run on a smartphone, which page is used to display a feed of the respectively assigned hub.

In the example embodiment according to FIG. 3, the GUI page 36 substantially has four display areas with a different function, namely a header 40, a search field 41, a display field 42 and a command bar 43. The header 40 mentions, by name, the hub 22-24 to which the application 31 is assigned. In the example of the application 31, the header 40 is therefore labeled with the word "patient hub", for example. Furthermore, the header 40 preferably mentions the facility 2 to which the system 1 is assigned.

The search field 41 contains an input line 44, which can be used to input an alphanumeric search term, and a button 45, the actuation of which by a user can start a search query Q on the basis of the search term previously input in the input line 44.

Additionally or alternatively, the search field 41 contains a preselection field 46 which can be used to select one or more preset search terms by tapping (in the case of a touch-sensitive screen) or clicking with a pointer device which is possibly present.

The search terms which can be generated using the preselection field 46 are, in particular, frequently used search schemes. For example, in the case of the application 31 corresponding to the patient hub 22, the preselection field 46 enables a preselection to the effect that
  all tweets 27 or
  only those tweets 27 relating to patients for which examinations are scheduled or
  only those tweets 27 relating to patients who have already been billed for the previous service
are intended to be returned as a feed 35.

Optionally, when generating a search term using the preselection field 46, provision is made for an alphanumeric equivalent of this search term to be automatically displayed in the input line 44.

The feed 35 returned on the basis of a search query Q is displayed in the display field 42. The display field 42 therefore contains, in the form of a list, those tweets 27 which have been found on the basis of the search query Q from the application 31 in the patient hub 22. A small image 47 and/or a keyword 48 is/are displayed, for example, for each tweet 27. In the case of the application 31 assigned to the patient hub 22, a small image of the patient and the name of the patient and optionally a patient identification number are preferably displayed for each displayed tweet 27. The search query Q and the feed 35 returned on the basis of the latter can be interactively changed by a user at the runtime of the application 31-33.

The search is defined on the basis of a syntax according to REST or OData (open data protocol standard). REST (representational state transfer) denotes in this case a programming paradigm for Internet applications which satisfies the following principles:
  each service offered is allocated a unique address (uniform resource locator: URL for short);
  the service accessible at an address can have different manifestations (representations);
  a stateless protocol is used which makes it possible to always handle different queries independently of one another;
  a predefined number of operations (namely, in particular, the four operations GET, POST, PUT, DELETE) with defined properties must be able to be applied to all resources;

multimedia hypertext (hypermedia) is used both for application information and for state changes.

In this case, representation is preferably effected according to the Internet standards XML (extensible markup language), JSON (Java script object notation) and/or ATOM. In this case, ATOM is used as an umbrella term for the atom syndication format (ASF), which is an XML format for interchanging messages, and the ATOM publishing protocol (APP) which is a programming interface for creating and processing web contents.

The search function is fundamentally similar to a WHERE clause according to the SQL standard. However, in contrast to the latter, it is not dependent on static re-indexing. In particular, the tables of a hub do not require any index elements for the search, which is why there is no need for any re-indexing either, and no separate data servers or database servers accordingly need to be kept either.

A tweet 27 displayed in the display field 42 can be selected by a user by simply tapping or clicking on this tweet 27.

The command bar 43 contains a number of buttons 49 and 50, the actuation of which by a user makes it possible to carry out elementary operations for controlling the user interface 37 and for managing and processing the displayed feed 35.

In the version illustrated in FIG. 3, the application 31 is optimized for display on the smartphone 12. In this case, only an individual GUI page 36 with an individual feed 35 is always displayed at any time on the smartphone 12. However, a plurality of instances of the GUI page 36 may be generated parallel to one another, these instances being executed concurrently on the smartphone 12 in the background of the display. A plurality of search queries Q can therefore be executed parallel to one another, in particular. The GUI pages 36 run in a generic frame 51 (or container). This frame 51 (and therefore the entire application 31) can be implemented, for example, as a separate application or as a plug-in for a web browser. Alternatively, however, the application 31 may also be designed for immediate running in a web browser, for example in the form of an HTML5 application.

In this case, the buttons 50 of the command bar 43 make it possible to change between the running GUI pages 36 by virtue of the displayed GUI page 36 being hidden from the user interface 37 and another GUI page 36 being displayed when one of the buttons 50 is actuated.

The further buttons 49 of the command line 43 are assigned, in particular, to the following CRUD functions:
"create": a new GUI page 36 of the user interface 37 is created in response to the actuation of the corresponding button 49;
"delete": the displayed GUI page 36 of the user interface 37 is ended in response to the actuation of the corresponding button 49;
"read": a GUI page 52—schematically illustrated in FIG. 4—of the user interface 37 is opened in response to the actuation of the corresponding button 49, which GUI page displays the data contents of the selected tweet 27 for mere inspection or for changing.

Figure 4:
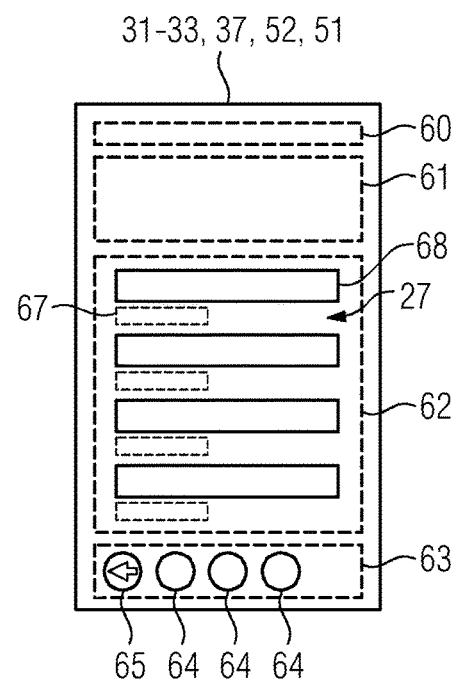
FIG. 4 shows, in an illustration according to FIG. 3, a further page of the user interface of the browser application, which page is used to display a tweet of the associated hub.

According to FIG. 4, the GUI page 52 likewise comprises four areas, namely a header 60, a title field 61, a display field 62 and a command bar 63.

In a similar manner to the header 40 of the GUI page 36, the header 60 in this case has the assigned hub 22-24 and the facility 2. The title field 61 indicates the type of data record displayed and therefore contains, for example, the word "patient" (or "patient entity") in the case of the application 31.

The contents of the selected tweet 27—therefore the contents of the (patient) data record in the case of the application 31—are presented in the display field 62. In this case, the field names 67 of the patient data record (for example "first name", "surname", "patient ID", "age", etc.), in particular, are presented together with the respective field contents 68 (that is to say, for example, specific first name, surname, the specific patient ID and the specific age of the patient) in the display field 62.

The command line 63 contains buttons 64 which are allocated, in particular, the following CRUD functions:
"create": a new instance of the GUI page 52 for creating a new tweet 27 and therefore a new (patient) data record P is created in response to the actuation of the corresponding button 64;
"update": the—possibly changed—field contents 68 are stored in response to the actuation of the corresponding button 64 by virtue of the application 31 immediately overwriting the displayed tweet 27 in the table storage 26 of the patient hub 22 with the changed details;
"delete": the displayed tweet 27 is immediately deleted by the application 31 in the table storage 26 of the patient hub 22 in response to the actuation of the corresponding button 64; the displayed GUT page 52 is closed.

In addition, the command line 63 contains a button 65, in response to the actuation of which the application 31 closes the displayed GUI page 52 without changing the tweet 27 and again displays the underlying GUI page 36.

The command lines 43 and 63 may have further buttons for commands. One or more of the functions described using the buttons 49, 50, 64 and 65 may also likewise be assigned to one of the possibly present electromechanical keys of the smartphone 12. In this case, the respective button is preferably removed from the command line 43.

The applications 32 and 33 are likewise browser applications which correspond to the application 31 in terms of their structure and the method of operation. In particular, the respective user interface 37 of the applications 32 and 33 also respectively has the GUI pages 36 and 52 described using FIGS. 3 and 4.

However, the applications 32 and 33 access the work list hub 23 and the context hub 24 and are accordingly adapted. In particular
the tweets 27 displayed within the scope of the application 32 therefore contain details of a particular task W (for example details of the set-up date of the task, the department entrusted, with the task, as well as details of the task itself and the task flow in which this task is possibly incorporated), and
the tweets 27 displayed within the scope of the application 33 therefore contain the contents of a respective context data record C, in particular details of the document type, storage location, data format and optionally recording parameters for an image data record B.

In an alternative embodiment (not illustrated in any more detail), two or even all three applications 31 to 33 are combined to form, a comprehensive application. This comprehensive application, comprises a common frame 51 in which a plurality of GUI pages 36 and/or 52 run, which pages are assigned to different resource hubs and are therefore used to display feeds 35 and tweets 37 of different data types. In the case of the applications 31-33, the frame 51 is configured, in particular, in such a manner that if can be configured using one or more of the individual browsing applications 31-33. As shown using the code example in the annex, the frame 51 and browsing applications 31-33 are preferably implemented as a container app and sub-apps in a single device application which can also run in a web browser as an HTML5 application.

Communication between each of the hubs 22-25 and the respectively allocated application 31-34 is configured—as indicated above—in such a manner that it is compatible with the REST (representational state transfer) principle customary in Internet data traffic. In particular, the data interchanged between the hubs 22-25 and the respective application 31-34 meet the XML, JSON and ATOM standards. Image data B are stored in the image hub 25 in the JPEG format, in particular, and volume data are preferably stored in the DICOM format. The views V (scene graphs) of volume data, which are possibly delivered to the application 34 by the public cloud 13 are preferably created in the JPEG format. Additionally or alternatively, however, image data and documents may also be stored in the image hub 25 in other data formats, for example webm, mp4, pdf or dz.

Each of the applications 31-33 is set up to externalize feeds 35 from the associated hub 22-24 into a local memory of the device 8 on the instructions of the user, with the result that this feed 35 and the tweets 27 contained therein can be displayed and/or processed by the application 31-33 even without a network connection to the public cloud 13. Furthermore, each application 31-33 is set up to transmit externalized feeds 35 or tweets 27 to another instance of the application or to another application 31-34 in response to a corresponding command from the user. In order to transmit the feeds 35 or tweets 27 inside the device, a local memory area which is referred to as an "exchange board" and is jointly accessed by all instances of the applications 31-34 is set up in the memory of the device 8. In order to be interchanged via the exchange board, the feeds 35 or tweets 27 to be interchanged are serialized in XML/JSON files which are stored in the local memory of the device 8 and are then deserialized again. In order to interchange feeds 35 or tweets 27 between different devices 8, the applications 31-34 preferably have interfaces to Twitter or an email program.

FIG. 5 shows a variant of the applications 31-33 in which the user interface 37 is optimized for display on a large-format screen, for example the screen 10 of the personal computer 9 or the screen of the tablet computer 11. The user interface 37 according to FIG. 5 differs from the user interface 37 shown in FIGS. 3 and 4 substantially in that a plurality of instances of the GUI pages 36 and/or 52 of the user interface 37 are presented beside one another and are therefore visible at the same time.

In the illustration according to FIG. 5, the user interface 37 also has additional navigation buttons 50, the actuation of which again makes it possible to browse between the displayed GUI pages 36 and/or 52.

In addition, the user interface 37 additionally has a menu line 80, the actuation of which makes it possible to change between the different applications 31-34. In this case, the menu line 80 is, in particular, part of a frame 81 (or container) in which the existing instances of the applications 31-34 run.

FIG. 6 schematically illustrates a model of the component architecture of one of the applications 31-33. It can be gathered from the illustration that the application 31-33 is formed from components which are arranged in five layers.

The hierarchically highest layer of this architecture is referred to as the frame layer 90. In the example according to FIG. 6, this frame layer 90 is formed by a frame component 91 which implements the frame 51 or 81. As becomes clear from FIGS. 3 to 5, the frame 51 or 81 (and therefore the frame component 91) determines how many GUI pages 36 or 52 are displayed at the same time, how these GUI pages 36, 52 are arranged on the screen surface and how control is transferred between the concurrently existing instances of the GUI pages 36 and 52, that is to say how these instances are activated and deactivated for user interaction and are displayed and hidden on the screen.

The frame component 91 is specifically selected on the basis of the type of device 8 on which the application 31-33 is intended to run and is tailored to the form factor of the respective device 8 (that is to say the size and geometry of the screen) and to the user interaction device present in the device 8. For example, a version of the frame component 91 intended to run on the tablet computer 11 or smartphone 12 supports user interaction methods as are conventional for user interaction using a touchscreen (for example shifting the GUI pages 36 and 52 by manually swiping across the screen, zooming the image information by way of two-finger operations, rotating the image information when tilting the device 8, etc.). In contrast, a version of the frame component 91 designed to run in a personal computer 9 preferably provides graphical control elements in the form of buttons in a manner adapted to user interaction using a mouse or touchpad.

Lying under the frame layer 90 is a view layer 92. In the case of the application 31-33, this view layer 92 comprises two components 93 and 94 which define the "view", that is to say the graphical configuration of the GUI pages 37. In this case, the component 93 defines the control elements of the GUI page 36 with respect to the type, appearance and arrangement. The component 94 accordingly defines the control elements of the GUI page 52.

The components 93 and 94 are specifically designed for the type of data records to be displayed, that is to say for patient data records P in the case of the application 31. In this respect, the components 93 and 94 of the application 31 are different from corresponding components 93 and 94 of the applications 32 and 33. If the application—unlike in FIG. 6—is designed to display a plurality of data types, the application respectively comprises two components for each data type to be displayed in the view layer 92, one of which components defines the GUI page 36 for displaying the associated feeds 35, while the other defines the GUI page 52 for displaying the associated tweets 27.

Below the view layer 92, the application 31-33 comprises two further components 96 and 97 in a view model layer 95. Each of these components 96 and 97 defines, for the respectively assigned, component 93 or 94 of the view layer 92, properties and commands for the control elements of the graphical user interface 37 which are defined in this component 93 or 94, in particular the CRUD functions described above. In this case, the components 96 and 97 of the view model layer 95 are generic, that is to say independent of the data type to be displayed. The components 96 and 97 are therefore also identical in all applications 31, 32 and 33.

Below the view model layer 95, the application 31-33 comprises a model layer 98. This model layer 98 comprises a component 99 which defines the structure of the data records to be displayed, that is to say the structure of the patient data records P in the case of the application 31. The component 99 in this case contains, in particular, the definitions for the variables of the respective data records, for example the "name", "first name", etc. in the case of the patient data records P.

A driver layer 100 is in turn arranged below the model layer 98. In this case, the driver layer 100 comprises one or more driver components 101 which provide access to the data records stored in a predefined data memory 102 and the assigned feeds 35 and tweets 27 for the superordinate layers.

Depending on the design of the driver component 101, the data memory 102 is either the local memory of the device 8, the table storage 26 or another memory of the assigned hub 22-24 or another external memory. In the generalized sense, the data memory 102 may also be an email or SMS receiver or a social network, in particular Twitter. In this case, the application 31-33 preferably comprises a plurality of different driver components 101 which are each assigned to a particular data memory 102.

All of the driver components 101 are based on a common, defined driver API 103. The driver components 101 are likewise generic, that is to say independent of the data type to be displayed.

Communication between the or each driver component 101 and the superordinate layers is effected asynchronously in this case. This means that the components of the superordinate layers do not wait for the response from the driver component 101 following a query for the driver component or one of the driver components 101, with the result that any delays when accessing the data records do not burden the running of the application 31.

As described above, a plurality of instances of the GUI pages 36 and 52 may be operated concurrently. Accordingly, as illustrated in FIG. 7, the components 93, 94, 96, 97, 99 of the view layer 92, of the view model layer 95 and of the model layer 98 can also be instantiated repeatedly and may run concurrently. The driver components 101 of the driver layer 100 can also be instantiated repeatedly, with the result that each instance of the GUI page 36 or 52 is assigned an associated instance of the driver component 101. The driver instances are operated concurrently and—as mentioned above—can access the same data memory 102 or different data memories 102.

The invention becomes particularly clear from the example embodiments described above but is nevertheless not restricted to the example embodiments. Rather, further embodiments of the invention may be derived from the present description and the claims. In particular, the individual features of the invention which are described using the example embodiments can also be combined in another manner without departing from the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject natter of independent claims or divisional declarations. They may furthermore also contain independent inventions which nave a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned, embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, fox example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The following annexes cite examples of a specific implementation of the application template, the driver API 103 and the component 97 of the view model layer 95.

LIST OF REFERENCE SYMBOLS

1 System
2, 2' (Medical) facility
3 Modality
4 Computer tomograph
5 C-arm device
6 Magnetic resonance tomograph
7 (Control and evaluation) computer
8 Device
9 Personal computer
10 Screen
11 Tablet computer
12 Smartphone
13 Public cloud
14 (Data transmission) network
15 Intranet
16 Internet
17 Firewall
18, 18' Subscription
19 Cloud storage
20 App store
21 Cloud computing service
22 (Patient) hub
23 (Work list) hub
24 (Context) hub
25 (Image) hub
26 Table storage
27 Tweet
28 Blob storage
29 URL
31 Application
32 Application
33 Application
34 Application
35 Peed
36 GUI page
37 (Graphical) user interface
40 Header
41 Search field
42 Display field
43 Command bar
44 Input line
45 Button
46 Preselection field
47 image
48 Keyword
49 Button
50 Button
51 Frame
52 GUI page
60 Header
61 Title
62 Display field
63 Command line
64 Button
65 Button
67 Field names
68 Field contents
69 Page
70 Header
71 Title
72 Display field
73 Command line
74 Button
80 Menu line
81 Frame
90 Frame layer
91 Frame component
92 view layer
93 Component
94 Component
95 View model layer
95 Component
97 Component
98 Model layer
99 Component
100 Driver layer
101 Driver component
102 Data memory
103 Driver API
P Patient data record
W Task
C Context data record
B Image data record
V View
Q Search query
R Query
K Key image

What is claimed is:
1. A system for managing and processing data in a medical facility, the system comprising:
a plurality of medical examination devices in the medical facility;
a plurality of different types of user devices in the medical facility that display and process data;
a public cloud outside of the medical facility storing downloadable applications, templates drivers, patient data records, patient image data records and patient associated tasks to be performed by the medical facility, the public cloud being connected to the plurality of medical examination devices and the plurality of different types of user devices;
at least one browser application installed on each of the plurality of different types of user devices configured to run on the user devices, the browser application being configured to access and display
data record lists, stored in the public cloud, containing a respective list entry for a number of medical data records of a particular data type including data inclusive of data generated by the plurality medical examination devices, data of hospital information systems (HIS), radiology information systems (RIS) and picture archiving and communication systems (PACS), and
individual list entries resulting from search queries via the browser application
for inspection and processing, the at least one browser application being subdivided into the following layers in terms of its component architecture:
a frame layer comprising at least one frame component, the frame component defining a number and arrangement of GUI pages to be displayed at the same time for a respective data record list or GUI pages for a respective list entry, and the frame component also being configured to implement functions for transferring control between different GUI pages,
a view layer comprising a number of components, each respectively specifically defining, for a particular data type, the graphical contents of a GUI page for displaying a data record list or a GUI page for displaying a list entry,
a view model layer comprising a number of components, each defining, for at least one associated component of the view layer, properties and commands for the control elements of the GUI page defined there, a model layer comprising a number of components, each respectively specifically defining, for a particular data type, the structure of the associated data records, and a driver layer comprising a number of driver components, each respectively configured to facilitate data access to a particular data memory inside or outside the user device, the components of the view model layer being independent of the data type.

2. The system of claim 1, wherein the driver components are independent of the data type.

3. The system of claim 2, wherein the at least one frame component is independent of the data type.

4. The system of claim 2, wherein the driver layer comprises an application programming interface on which at least one driver component is based.

5. The system of claim 2, wherein the components of the view model layer comprise generic functions for creating, reading, updating and deleting data record lists or individual list entries.

6. The system of claim 1, wherein the at least one frame component is independent of the data type.

7. The system of claim 1, wherein the driver layer comprises an application programming interface on which at least one driver component is based.

8. The system of claim 1, wherein the components of the view model layer comprise generic functions for creating, reading, updating and deleting data record lists or individual list entries.

9. The system of claim 1, wherein the at least one browser application is set up to display data record lists and list entries for data records of the following data types:

patient data, each data record of which respectively contains personal and medical data relating to a particular patient, tasks or work lists, each data record of which contains a task or sequence of tasks to be carried out by a medical user, context data, each data record of which contains context information relating to a medical image data record.

10. The system of claim 9, wherein, the context information relating to a medical image data record is a reference to the storage location of the image data record.

11. The system of claim 1, wherein the at least one browser application is set up to directly access at least one of data records and their associated list entries in a data memory arranged outside the user device.

12. The system of claim 11, wherein the browser application is set up to directly access at least one of data records and their associated list entries in a cloud storage of a public cloud, without using an interposed server.

13. The system of claim 1, further comprising:

an application template stored in the public cloud, the application template being common to each of the plurality of different types of user devices and an application configurator, the application configurator being independent of the at least one browser application and configured to automatically generate a browser application for each of the plurality of different types of user devices from the application template using predefined configuration information, the configuration information comprising at least one of:

details relating to the type of user device on which the respective browser application is intended to run, details relating to the at least one particular data type of the data records, the associated list entries and data record lists of which are intended to be displayed and processed using the respective browser application, and details relating to the particular data memory which is intended to be accessed by the respective browser application.

14. The system of claim 1, wherein at least one driver component is able to be instantiated repeatedly.

15. The system of claim 1, wherein the data access by at least one driver component is provided asynchronously and independently of the other driver components.

16. The system of claim 1, wherein the at least one browser application includes a plurality of browser applications, each of the browser applications being linked to a respective hub in cloud storage, and each hub comprising data specific to a respective one of the plurality of browser applications.

* * * * *